United States Patent
Lorenzo

(10) Patent No.: US 10,639,043 B2
(45) Date of Patent: *May 5, 2020

(54) VASCULATURE OCCLUSION DEVICE DETACHMENT SYSTEM WITH TAPERED COREWIRE AND HEATER ACTIVATED FIBER DETACHMENT

(71) Applicant: DePuy Synthes Products, Inc., Raynham, MA (US)

(72) Inventor: Juan A. Lorenzo, Davie, FL (US)

(73) Assignee: DePuy Synthes Products, INC., Raynham, MA (US)

( * ) Notice: Subject to any disclaimer, the term of this patent is extended or adjusted under 35 U.S.C. 154(b) by 380 days.

This patent is subject to a terminal disclaimer.

(21) Appl. No.: 15/648,370

(22) Filed: Jul. 12, 2017

(65) Prior Publication Data

US 2017/0303931 A1     Oct. 26, 2017

Related U.S. Application Data

(63) Continuation of application No. 14/491,109, filed on Sep. 19, 2014, now Pat. No. 9,782,178.

(51) Int. Cl.
    *A61B 17/12*     (2006.01)
    *A61B 17/00*     (2006.01)

(52) U.S. Cl.
    CPC .... *A61B 17/12109* (2013.01); *A61B 17/1214* (2013.01); *A61B 17/12022* (2013.01);
    (Continued)

(58) Field of Classification Search
    None
    See application file for complete search history.

(56) References Cited

U.S. PATENT DOCUMENTS 5,522,836 A * 6/1996 Palermo ........... A61B 17/12022
                                                        606/108
5,669,905 A     9/1997 Scheldrup et al.
(Continued)

FOREIGN PATENT DOCUMENTS

CN    203591293    5/2014
EP    1806105      7/2007
(Continued)

OTHER PUBLICATIONS

Co-pending, co-owned U.S. Appl. No. 14/491,109, filed Sep. 19, 2014.
(Continued)

*Primary Examiner* — Shaun L David
(74) *Attorney, Agent, or Firm* — Cohen & Hildebrand, PLLC

(57) ABSTRACT

A vasculature occlusion device detachment system including a wound coil heating element of a predetermined resistivity. A coil securing suture terminates in a proximal bead retained within the wound coil heating element while the distal end of the coil securing suture extends beyond the distal end of the wound coil heating element and is attached to the proximal end of the vasculature occlusion device. The coil securing suture is independently rotatable of the wound coil heating element 360 degrees about a longitudinal axis extending therethrough the wound coil heating element. A power source applies electrical current to the wound coil heating element via an electrically conductive corewire and separate insulated electrically conductive wire to increase its resistance and, as a result of the heat produced, sever the coil securing suture.

12 Claims, 9 Drawing Sheets

(52) U.S. Cl.
CPC .. *A61B 17/12113* (2013.01); *A61B 17/12154* (2013.01); *A61B 2017/00929* (2013.01); *A61B 2017/1209* (2013.01); *A61B 2017/12068* (2013.01)

(56) References Cited

U.S. PATENT DOCUMENTS

| | | | |
|---|---|---|---|
| 5,725,534 | A | 3/1998 | Rasmussen |
| 5,853,418 | A | 12/1998 | Ken et al. |
| 6,013,084 | A | 1/2000 | Ken et al. |
| 6,063,100 | A | 5/2000 | Diaz et al. |
| 6,179,857 | B1 | 1/2001 | Diaz et al. |
| 6,193,728 | B1 | 2/2001 | Ken et al. |
| 6,280,457 | B1 | 8/2001 | Wallace et al. |
| 6,425,914 | B1 | 7/2002 | Wallace et al. |
| 6,458,127 | B1 | 10/2002 | Truckai et al. |
| 6,478,773 | B1 | 11/2002 | Gandhi et al. |
| 6,743,236 | B2 | 6/2004 | Barry et al. |
| 6,866,677 | B2 | 3/2005 | Douk et al. |
| 6,953,473 | B2 | 10/2005 | Porter |
| 6,966,892 | B2 | 11/2005 | Gandhi et al. |
| 7,255,707 | B2 | 8/2007 | Ramzipoor et al. |
| 7,331,973 | B2 | 2/2008 | Gesswein et al. |
| 7,582,101 | B2 | 9/2009 | Jones et al. |
| 7,651,513 | B2 | 1/2010 | Teoh et al. |
| 7,722,637 | B2 | 5/2010 | Barry et al. |
| 7,740,637 | B2 | 6/2010 | Gandhi et al. |
| 8,100,918 | B2 | 1/2012 | Gandhi et al. |
| RE43,311 | E | 4/2012 | Wallace et al. |
| 8,182,506 | B2 | 5/2012 | Fitz et al. |
| 8,273,116 | B2 | 9/2012 | Licata et al. |
| 8,298,256 | B2 | 10/2012 | Gandhi et al. |
| 8,328,860 | B2 | 12/2012 | Strauss et al. |
| 8,945,024 | B2 | 2/2015 | Takata et al. |
| 9,532,792 | B2 | 1/2017 | Galdonik et al. |
| 9,532,873 | B2 | 1/2017 | Kelley |
| 9,533,344 | B2 | 1/2017 | Monetti et al. |
| 9,539,011 | B2 | 1/2017 | Chen et al. |
| 9,539,022 | B2 | 1/2017 | Bowman |
| 9,539,122 | B2 | 1/2017 | Burke et al. |
| 9,539,382 | B2 | 1/2017 | Nelson |
| 9,549,830 | B2 | 1/2017 | Bruszewski et al. |
| 9,554,805 | B2 | 1/2017 | Tompkins et al. |
| 9,561,125 | B2 | 2/2017 | Bowman et al. |
| 9,572,982 | B2 | 2/2017 | Burnes et al. |
| 9,579,484 | B2 | 2/2017 | Barnell |
| 9,585,642 | B2 | 3/2017 | Dinsmoor et al. |
| 9,615,832 | B2 | 4/2017 | Bose et al. |
| 9,615,951 | B2 | 4/2017 | Bennett et al. |
| 9,622,753 | B2 | 4/2017 | Cox |
| 9,636,115 | B2 | 5/2017 | Henry et al. |
| 9,636,439 | B2 | 5/2017 | Chu et al. |
| 9,642,675 | B2 | 5/2017 | Werneth et al. |
| 9,655,633 | B2 | 5/2017 | Leynov et al. |
| 9,655,645 | B2 | 5/2017 | Staunton |
| 9,655,989 | B2 | 5/2017 | Cruise et al. |
| 9,662,129 | B2 | 5/2017 | Galdonik et al. |
| 9,662,238 | B2 | 5/2017 | Dwork et al. |
| 9,662,425 | B2 | 5/2017 | Lilja et al. |
| 9,668,898 | B2 | 6/2017 | Wong |
| 9,675,477 | B2 | 6/2017 | Thompson |
| 9,675,782 | B2 | 6/2017 | Connolly |
| 9,676,022 | B2 | 6/2017 | Ensign et al. |
| 9,692,557 | B2 | 6/2017 | Murphy |
| 9,693,852 | B2 | 7/2017 | Lam et al. |
| 9,700,262 | B2 | 7/2017 | Janik et al. |
| 9,700,399 | B2 | 7/2017 | Acosta-Acevedo |
| 9,717,421 | B2 | 8/2017 | Griswold et al. |
| 9,717,500 | B2 | 8/2017 | Tieu et al. |
| 9,717,502 | B2 | 8/2017 | Teoh et al. |
| 9,724,103 | B2 | 8/2017 | Cruise et al. |
| 9,724,526 | B2 | 8/2017 | Strother et al. |
| 9,750,565 | B2 | 9/2017 | Bloom et al. |
| 9,757,260 | B2 | 9/2017 | Greenan |
| 9,764,111 | B2 | 9/2017 | Gulachenski |
| 9,770,251 | B2 | 9/2017 | Bowman et al. |
| 9,770,577 | B2 | 9/2017 | Li et al. |
| 9,775,621 | B2 | 10/2017 | Tompkins et al. |
| 9,775,706 | B2 | 10/2017 | Peterson et al. |
| 9,775,732 | B2 | 10/2017 | Khenansho |
| 9,788,800 | B2 | 10/2017 | Mayoras, Jr. |
| 9,795,391 | B2 | 10/2017 | Saatchi et al. |
| 9,801,980 | B2 | 10/2017 | Karino et al. |
| 9,808,599 | B2 | 11/2017 | Bowman et al. |
| 9,833,252 | B2 | 12/2017 | Sepetka et al. |
| 9,833,604 | B2 | 12/2017 | Lam et al. |
| 9,833,625 | B2 | 12/2017 | Waldhauser et al. |
| 2004/0002732 | A1 | 1/2004 | Teoh et al. |
| 2004/0034363 | A1 | 2/2004 | Wilson |
| 2004/0220563 | A1 | 11/2004 | Eder |
| 2005/0149108 | A1 | 7/2005 | Cox |
| 2005/0165439 | A1 | 7/2005 | Weber et al. |
| 2006/0135986 | A1 | 6/2006 | Wallace |
| 2007/0112375 | A1 | 5/2007 | Aganon et al. |
| 2008/0228215 | A1 | 9/2008 | Strauss |
| 2009/0177261 | A1 | 7/2009 | Teoh et al. |
| 2010/0030200 | A1 | 2/2010 | Strauss |
| 2010/0063572 | A1 | 3/2010 | Teoh et al. |
| 2010/0106162 | A1 | 4/2010 | Jaeger et al. |
| 2010/0234872 | A1 | 9/2010 | Guo |
| 2011/0301686 | A1 | 12/2011 | Bowman |
| 2012/0209310 | A1 | 8/2012 | Chen |
| 2012/0330349 | A1 | 12/2012 | Jones et al. |
| 2013/0138136 | A1 | 5/2013 | Beckham |
| 2013/0197547 | A1 | 8/2013 | Guo et al. |
| 2014/0277092 | A1 | 9/2014 | Teoh et al. |
| 2014/0277093 | A1 | 9/2014 | Guo et al. |
| 2015/0335333 | A1 | 11/2015 | Jones |
| 2017/0007264 | A1 | 1/2017 | Cruise et al. |
| 2017/0007265 | A1 | 1/2017 | Guo et al. |
| 2017/0020670 | A1 | 1/2017 | Murray et al. |
| 2017/0020700 | A1 | 1/2017 | Bienvenu et al. |
| 2017/0027640 | A1 | 2/2017 | Kunis et al. |
| 2017/0027692 | A1 | 2/2017 | Bonhoeffer et al. |
| 2017/0027725 | A1 | 2/2017 | Argentine |
| 2017/0035436 | A1 | 2/2017 | Morita |
| 2017/0035567 | A1 | 2/2017 | Duffy |
| 2017/0042548 | A1 | 2/2017 | Lam |
| 2017/0049596 | A1 | 2/2017 | Schabert |
| 2017/0071737 | A1 | 3/2017 | Kelley |
| 2017/0072452 | A1 | 3/2017 | Monetti et al. |
| 2017/0079671 | A1 | 3/2017 | Morero et al. |
| 2017/0079680 | A1 | 3/2017 | Bowman |
| 2017/0079766 | A1 | 3/2017 | Wang et al. |
| 2017/0079767 | A1 | 3/2017 | Leon-Yip |
| 2017/0079812 | A1 | 3/2017 | Lam et al. |
| 2017/0079817 | A1 | 3/2017 | Sepetka et al. |
| 2017/0079819 | A1 | 3/2017 | Pung et al. |
| 2017/0079820 | A1 | 3/2017 | Lam et al. |
| 2017/0086851 | A1 | 3/2017 | Wallace et al. |
| 2017/0086996 | A1 | 3/2017 | Peterson et al. |
| 2017/0095259 | A1 | 4/2017 | Tompkins et al. |
| 2017/0100126 | A1 | 4/2017 | Bowman et al. |
| 2017/0100141 | A1 | 4/2017 | Morero et al. |
| 2017/0100143 | A1 | 4/2017 | Grandfield |
| 2017/0100183 | A1 | 4/2017 | Iaizzo et al. |
| 2017/0113023 | A1 | 4/2017 | Steingisser et al. |
| 2017/0147765 | A1 | 5/2017 | Mehta |
| 2017/0151032 | A1 | 6/2017 | Loisel |
| 2017/0165062 | A1 | 6/2017 | Rothstein |
| 2017/0165065 | A1 | 6/2017 | Rothstein et al. |
| 2017/0165454 | A1 | 6/2017 | Tuohy et al. |
| 2017/0172581 | A1 | 6/2017 | Bose et al. |
| 2017/0172766 | A1 | 6/2017 | Vong et al. |
| 2017/0172772 | A1 | 6/2017 | Khenansho |
| 2017/0189033 | A1 | 7/2017 | Sepetka et al. |
| 2017/0189035 | A1 | 7/2017 | Porter |
| 2017/0215902 | A1 | 8/2017 | Leynov et al. |
| 2017/0216484 | A1 | 8/2017 | Cruise et al. |
| 2017/0224350 | A1 | 8/2017 | Shimizu et al. |
| 2017/0224355 | A1 | 8/2017 | Bowman et al. |
| 2017/0224467 | A1 | 8/2017 | Piccagli et al. |
| 2017/0224511 | A1 | 8/2017 | Dwork et al. |
| 2017/0224953 | A1 | 8/2017 | Tran et al. |

(56) References Cited

U.S. PATENT DOCUMENTS

| | | |
|---|---|---|
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |

FOREIGN PATENT DOCUMENTS

| | | |
|---|---|---|
| EP | 2644129 | 10/2013 |
| EP | 2644130 | 10/2013 |
| JP | 2013212372 | 10/2013 |
| JP | 2013212373 | 10/2013 |
| WO | 158366 | 8/2001 |
| WO | 2006046652 | 4/2006 |

OTHER PUBLICATIONS

Co-pending, co-owned U.S. Appl. No. 14/491,145, filed Sep. 19, 2014.

"Electricaly Resistivity and Conductivity"—Wikipedia—Revision of Jul. 20, 2014. Accessed on Wikipedia on Sep. 15, 2016 at https://en.Wikipedia.org/w/index.php?title=Electrical_resistivity_and_conductivity&diff=617665297&olded=614492869.

Japanese Office Action dated Jun. 18, 2019 (3 pages).

* cited by examiner

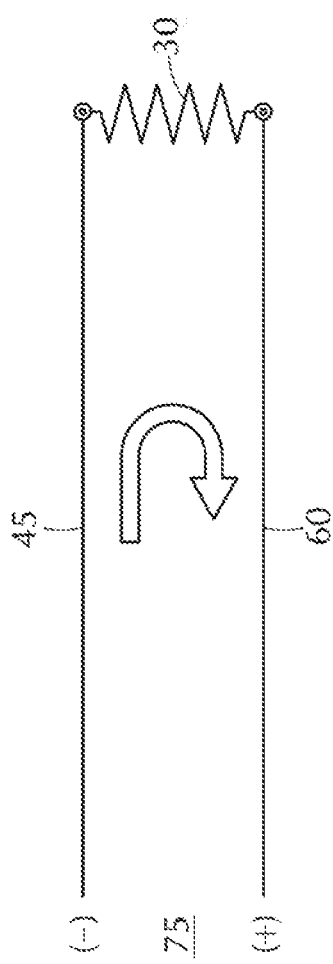

VASCULATURE OCCLUSION DEVICE DETACHMENT SYSTEM WITH TAPERED COREWIRE AND HEATER ACTIVATED FIBER DETACHMENT

CROSS-REFERENCE TO RELATED APPLICATIONS

This application is a continuation application of U.S. patent application Ser. No. 14/491,109, filed Sep. 19, 2014, now U.S. Pat. No. 9,782,178 B2 issued on Oct. 10, 2017, which is herein incorporated by reference in its entirety.

BACKGROUND OF THE INVENTION

Field of the Invention

The present invention relates to vasculature occlusive devices (e.g., embolic coils) for implantation within a blood vessel of a body. In particular, the present invention relates to an improved heating detachment system for an embolic coil delivery system in the treatment of blood vessel disorders.

Description of Related Art

Vascular disorders and defects such as aneurysms and other arterio-venous malformations are especially difficult to treat when located near critical tissues or where ready access to malformation is not available. Both difficulty factors apply especially to cranial aneurysms. Due to the sensitive brain tissue surrounding cranial blood vessels and the restricted access, it is very challenging and often risky to surgically treat defects of the cranial vasculature.

Alternative treatments include vasculature occlusion devices, such as embolic coils, deployed using catheter delivery systems. In such systems used to treat cranial aneurysms, the distal end of an embolic coil delivery catheter is inserted into non-cranial vasculature of a patient, typically through a femoral artery in the groin, and guided to a predetermined delivery site within the cranium.

Multiple embolic coils of various lengths, generally approximately 1 cm to as long as approximately 100 cm, and preselected stiffness often are packed sequentially within a cranial aneurysm to limit blood flow therein and to encourage embolism formation. Typically, physicians first utilize stiffer coils to establish a framework within the aneurysm and then select more flexible coils to fill spaces within the framework. Ideally, each coil conforms both to the aneurysm and to previously implanted coils. Each successive coil is selected individually based on factors including stiffness, length, and preformed shape which the coil will tend to assume after delivery.

During implantation, the physician manipulates each embolic coil until it is in a satisfactory position, as seen by an imaging technique such as fluoroscopic visualization, before detaching the coil from the delivery system. It is beneficial for both ends of each coil to remain positioned within the aneurysm after delivery; otherwise, a length of coil protruding into the main lumen of the blood vessel invites undesired clotting external to the aneurysm. After each successive coil is detached, the next coil is subject to an increasing risk of becoming entangled in the growing mass of coils, thereby restricting the depth of insertion for that coil into the aneurysm.

Difficulties may arise due to stretching of the embolic coils during repositioning or attempted retrieval of the coils, especially if the coil becomes entangled and complete insertion of the coil into the aneurysm is not accomplished. If pulling forces applied to a coil exceed its elastic limit, the coil will not return to its original shape. A stretched coil exhibits diminished pushability or retractability, and becomes more difficult to manipulate into an optimal position or to be removed. Moreover, a stretched coil occupies less volume than an unstretched coil, which increases the number of coils needed to sufficiently pack the aneurysm to encourage formation of a robust embolus positioned wholly within the aneurysm. To avoid such problems stretch resistance devices are used, such as that disclosed in U.S. Pat. No. 5,853,418, herein incorporated by reference in its entirety, having a primary coil and an elongated stretch-resisting member fixedly attached to the primary coil in at least two locations.

In order to deliver the vaso-occlusive coils to a desired site, e.g., an aneurysm, in the vasculature, it is well-known to first position a small profile, delivery catheter or microcatheter at the targeted site using fluoroscopy, ultrasound, or other method of steerable navigation. A delivery or "pusher" wire is then passed through a proximal end of the catheter lumen, until a vaso-occlusive coil coupled to a distal end of the pusher wire is extended out of the distal end opening of the catheter and into the blood vessel at the targeted site. The vaso-occlusive device is then released or detached from the end pusher wire, and the pusher wire is withdrawn in a proximal direction back through the catheter. Depending on the particular needs of the patient, another occlusive device may then be pushed through the catheter and released at the same site in a similar manner.

Several conventional methods are used to detach the wire from the embolic coil once it has been properly positioned at the targeted site in the blood vessel. One known way to release a vaso-occlusive coil from the end of the pusher wire is through the use of an electrolytically severable junction, which is an exposed section or detachment zone located along a distal end portion of the pusher wire. The detachment zone is typically made of stainless steel and is located just proximal of the vaso-occlusive device. An electrolytically severable junction is susceptible to electrolysis and disintegrates when the pusher wire is electrically charged in the presence of an ionic solution, such as blood or other bodily fluids. Thus, once the detachment zone exits out of the catheter distal end and is exposed in the vessel blood pool of the patient, a current applied to the conductive pusher wire completes a circuit with an electrode attached to the patient's skin, or with a conductive needle inserted through the skin at a remote site, and the detachment zone disintegrates due to electrolysis.

One disadvantage of occlusive devices that are deployed using electrolytic detachment is that the electrolytic process requires a certain amount of time to elapse to effectuate release of the occlusive element. This time lag is also disadvantageous for occlusive delivery devices that utilize thermal detachment such as that described in U.S. Pat. No. 6,966,892, which is herein incorporated by reference in its entirety.

Another conventional detachment technique during delivery of a vaso-occlusive device involves the use of fluid pressure (e.g., hydraulic detachment) to release an embolic coil once it is properly positioned, as described in U.S. Pat. Nos. 6,063,100 and 6,179,857, each of which is herein incorporated by reference in their entirety.

The main problems associated with current detachment schemes are reliability of detachment, speed of detachment, convenience of detaching mechanism (e.g., hydraulic detachment requires a high pressure syringe, while electrolytic detachment requires a battery operated box), and length/stiffness of the distal section.

It is therefore desirable to develop an improved heating detachment system for a vaso-occlusive device (e.g., an embolic coil device) that solves the aforementioned problems associated with conventional devices.

SUMMARY OF THE INVENTION

An aspect of the present invention relates to an improved heating detachment system for delivery of a vaso-occlusive device that is simpler, more reliable, quicker, more convenient and having a reduced length rigid distal section relative to that of conventional mechanical detachment systems.

Another aspect of the present invention is directed to an improved detachment system for delivery of a vaso-occlusive device that optimizes distal flexibility, placement at a desired treatment site and detachment characteristics.

Still another aspect of the present invention relates to a vasculature occlusion device detachment system including a heating element of a predetermined resistivity. A coil securing suture has proximal end that terminates in a proximal bead retained within the heating element while a distal end of the coil securing suture extends beyond the distal end of the heating element. The coil securing suture is rotatable independently of the heating element 360 degrees about a longitudinal axis extending therethrough the heating element. An electrically conductive corewire is connected at its distal end to the proximal end of the heating element. Separate from the electrically conductive corewire, an insulated electrically conductive wire is also secured at its distal end to the heating element at a heating-element-to-conductive wire connection.

Yet another aspect of the present invention is directed to a method of using the vasculature occlusion device detachment system in accordance with the preceding paragraph. The distal end of the coil securing suture is secured to a proximal end of a vasculature occlusion device. Then the vasculature occlusion device is advanced via a delivery catheter through a human body using the electrically conductive corewire. The vasculature occlusion device is positioned at a target site the human body. An electrical current powered by a power source is applied to the electrically conductive corewire and insulated electrically conductive wire. As a result of the applied electrical current, a resistance of the heating element is increased in a region of the heating-element-to-conductive wire connection. Sufficient heat is generated due to the increased resistance to melt and sever the coil securing suture at the region proximate the heating-element-to-conductive wire connection thereby releasing the vasculature occlusive device from the heating element. Lastly, the delivery catheter along with the heating element and the electrically conductive corewire are withdrawn from the human body by pulling in a proximal direction, while leaving at the target site in the human body the vasculature occlusive device.

BRIEF DESCRIPTION OF THE DRAWING

The foregoing and other features of the present invention will be more readily apparent from the following detailed description and drawings of illustrative embodiments of the invention wherein like reference numbers refer to similar elements throughout the several views and in which:

FIG. 1C is a schematic diagram of an electrical circuit formed by the power supply, the electrically conductive corewire, the insulated electrically conductive wire and the resistive heating element;

DETAILED DESCRIPTION OF THE INVENTION

The terms "proximal"/"proximally" and "distal"/"distally" refer to a direction closer to or away from, respectively, an operator (e.g., surgeon, physician, nurse, technician, etc.) who would insert the medical device into the patient, with the tip-end (i.e., distal end or leading end) of the device inserted inside a patient's body. Thus, for example, a "proximal direction" would refer to the direction towards the operator, whereas "distal direction" would refer to the direction away from the operator towards the leading or tip-end of the medical device.

By way of illustrative example only, the present inventive heating detachment system is utilized for delivery of an embolic component, e.g., embolic helical coil. It is, however, intended and within the scope of the present invention to use the present inventive heating detachment system with any type of vaso-occlusive device.

Figure 1A:
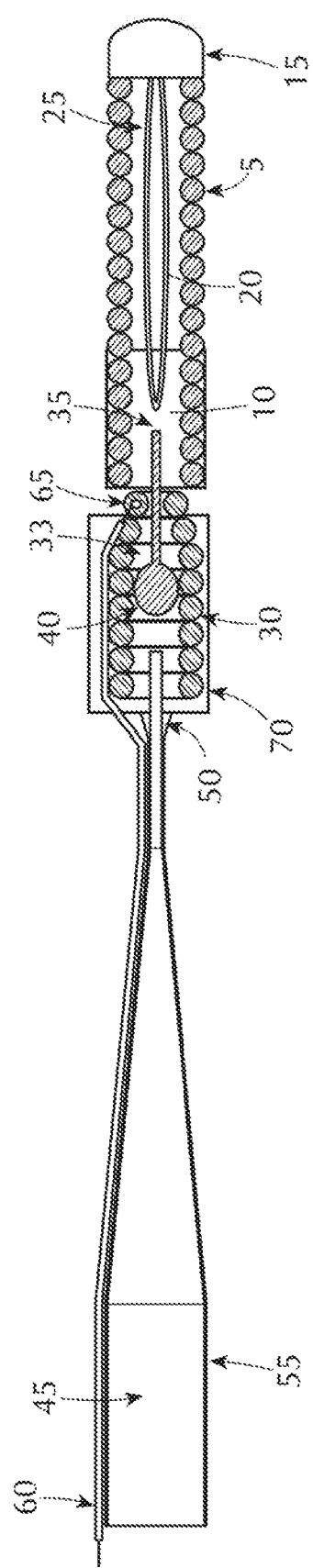
FIG. 1A is a cross-sectional view of a first embodiment of the present inventive heating detachment system for an embolic coil.

FIG. 1A is a cross-sectional view of a first exemplary heating detachment system in accordance with the present invention for delivery of a vaso-occlusive device, typically a helical embolic coil 5 formed by a series of loops/windings defining a coil lumen 25. The present inventive detachment system is not limited to embolic coils, but instead is equally suited for any type or shape vaso-occlusive device. Embolic coil 5 has a proximal coil junction 10 located at its proximal end. Proximal coil junction 10 is a joint, preferably made out of at least one of an adhesive, an epoxy and/or a polymer. Most preferably, the joint made of adhesive, epoxy and/or polymer is of relatively low strength and/or relatively low durometer. That is, the relatively low strength of the epoxy/adhesive, or the relatively low durometer of the polymer used to fill that junction (which is related to its tear-out strength) is preferably less than the buckling strength of a delivery catheter used to implant the vaso-occlusive device in a blood vessel. Opposite its proximal end, a distal end of the embolic coil 5 is closed off by a distal bead 15. One or more stretch resistant (SR) members 20, e.g., suture filaments, disposed in the coil lumen 25 provide stretch resistance when excessive pulling forces are applied to the embolic coil 5 during implantation in a patient. Preferably, each stretch resistant member 20 extends longitudinally the entire length of the coil lumen 25 secured at its respective ends by the proximal coil junction 10 and distal bead 15 to minimize excessive elongation.

Figure 1B:
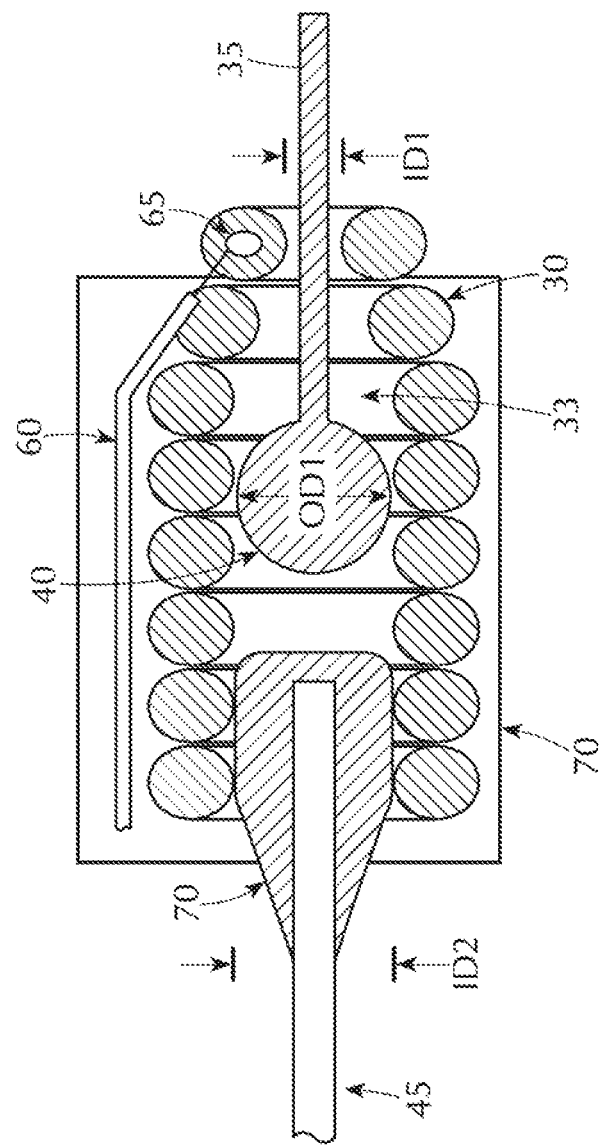
FIG. 1B is enlarged portion of the cross-sectional view of the heating detachment system for an embolic coil shown in FIG. 1A.

A heating element 30 of a given resistivity such as a conductive wire is preferably configured as a helically wound coil formed by a series of loops/windings. The helically wound coil is substantially flush at both its proximal and distal ends with a central lumen 33 defined longitudinally/axially therethrough. The helically wound coil is formed so that its proximal section inner diameter (ID2) is larger than its distal section inner diameter (ID1), as illustrated in FIG. 1B.

The heating element 30 is independent of the embolic coil 5 so that the two components may, independent of one another, freely rotate 360 degrees about a common longitudinal axis extending axially through the two components. The distal section of the heating element 30 proximate its distal end has reduced inner diameter (ID1) of its distal windings relative to that of the inner diameter (ID2) of its proximal section. Rather than be directly connected (i.e., in direct physical contact) to one another, heating element 30 and embolic coil 5 are indirectly linked to one another via a coil securing suture 35 made, for example, of a temperature sensitive polymer, disposed within the central lumen 33 of the heating element 30. Preferably there is only a single coil securing suture 35, however, more than one coil securing suture 35 may be employed, as desired. A distal end of the coil securing suture 35 has a diameter sufficiently small to pass through the distal section inner diameter (ID1) and extend beyond the distal end of the heating element 30 where it is embedded or otherwise secured via mechanical, adhesive and/or other means to a proximal coil junction 10 of the embolic coil 5. An opposite proximal end of the coil securing suture 35 terminates in a proximal bead 40 of a shape and dimension so as to move freely in an axial direction within the central lumen 33 of the heating element 30. Preferably the proximal bead is a sphere whose outer diameter (OD1) is smaller than the proximal section inner diameter (ID2) of the heating element 30. The coil securing suture 35 is not connected, secured or attached in any way to the heating element 30. Specifically, the outer diameter (OD1) of the proximal bead 40 of the coil securing suture 35 is smaller than the proximal section inner diameter (ID2) of the heating element 30 providing sufficient clearance for the proximal bead 40 to move freely in an axial direction within the central lumen 33 of the heating coil 30. As depicted in the enlarged illustration shown in FIG. 1B, the outer diameter (OD1) of the proximal bead 40 of the coil securing suture 35 is greater than the distal section inner diameter (ID1) of the heating element 30 and hence prevented from passing through the distal section of the heating element 30. Accordingly, proximal bead 40 retained within the central lumen 33 by its larger diameter relative to the narrow inner diameter of the distal section of the heating element prevents heating element 30 from separating from the embolic coil 5 until the coil securing suture 35 melts and severs or separates.

Figure 1D:
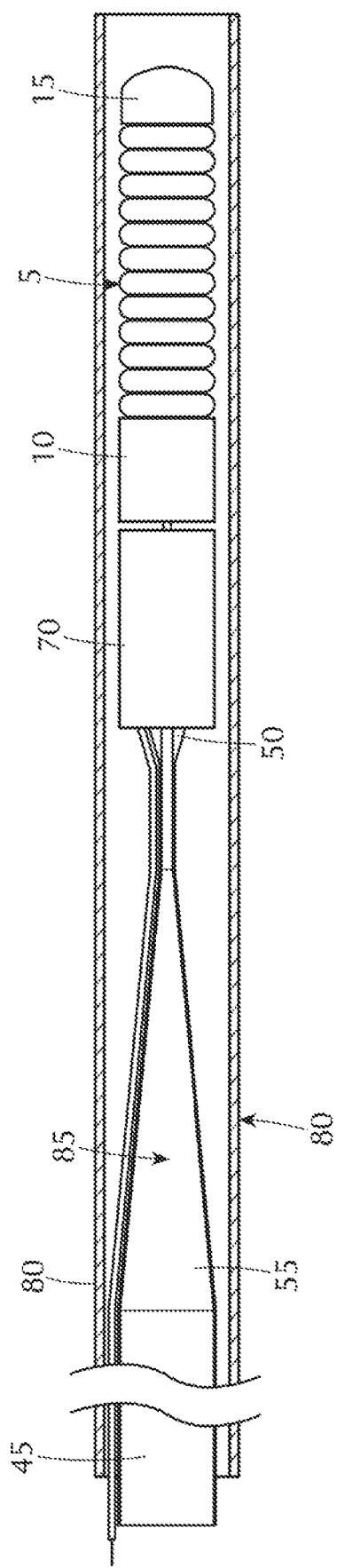
FIG. 1D is a side view of the delivery catheter with the first embodiment of the present inventive attachment system for an embolic coil assembled therein.

Referring to FIG. 1D, embolic coil 5 is advanced through a delivery catheter 80 by a delivery system 85 including corewire 45 to a target site in the blood vessel. In contrast to conventional pusher members having a central lumen, there is no central lumen defined longitudinally through corewire 45. Instead, an electrically conductive corewire (e.g., ground delivery wire) 45 is embedded, connected, attached, mounted or otherwise secured at its distal end to the proximal end of the heating element 30 via a corewire-to-heating-element joint 50 (e.g., solder, adhesive or epoxy) extending longitudinally partially into the proximal end of the central lumen 33 of the heating element 30. For a more secure attachment, the corewire-to-heating-element joint 50 disposed about the exterior of the corewire 45 may possibly extend longitudinally in a proximal direction beyond the heating element 30. Corewire 45 has a stiffer proximal section proximate its proximal end compared to its more flexible distal section proximate its distal end. As is illustrated in FIG. 1A, flexibility of the corewire 45 needed to advance the delivery system 85 through distal tortuosity may be achieved by grinding tapers over its distal section, wherein the length and/or number of tapers determines the flexibility of the distal section. Thus, the length and/or number of tapers shown in the drawings is for illustrative purposed only and may be adapted, as desired. The corewire is made from any biocompatible electrically conductive material such as stainless steel or Nitonal. Corewire 45 may be made either as an integrated single piece construction throughout or, alternatively, as a two-piece construction secured, attached, connected or mounted together. For instance, the proximal section of the corewire may be a first material (e.g., stainless steel), while the distal section connected to the proximal section may be made of a second material (e.g., Nitonal) different than the first material. A non-conductive coating (e.g., insulation sleeve) 55 is disposed about the exterior of the corewire 45.

Attached, secured, connected or otherwise mounted to its outer surface and extending preferably the length of the insulated corewire 45 is an insulated electrically conductive wire 60. As illustrated in FIG. 1B, a distal end of the insulated electrically conductive wire 60 is stripped of its insulation (as depicted by its thinner diameter) and electrically connected to the distal end of the heating element 30 at a heating-element-to-conductor-wire connection 65, for example, by solder, welding, or conductive epoxy. Protective sleeve 70 preferably encases a portion of both the heating element 30 and the insulated electrically conductive wire 60 coinciding with the heating element. The only portion of the heating element 30 not encased by the protective sleeve 70 is its distal end where the heating-element-to-conductor-wire connection 65 is located.

Once the embolic coil 5 has been properly positioned at a desired treatment site within the blood vessel, electrical activation of the heating element 30 by a power source (e.g., a battery) 75 produces heat in a region of the heating-element-to-conductor-wire connection 65 causing the coil securing suture 35 to melt and thus sever thereby releasing the embolic coil 5 secured to its distal end. In operation, once the embolic coil has been delivered by a catheter to a desired treatment site within the blood vessel, detachment occurs by applying an electrical current powered by the power source (e.g., battery) 75. In turn, the resistivity of the heating element increases resulting in a rise in temperature in a region of the heating-element-to-conductor-wire connection 65 at the distal end of the heating element 30 causing the coil securing suture 35 to melt and thus sever, thereby releasing the embolic coil 5. In the schematic diagram electrical circuit shown in FIG. 1C, a power supply 75 is connected across the conductors (i.e., proximal ends of corewire 45 and insulated electrically conductive wire 60) thereby applying a current across the resistive heating element 30 which converts electrical energy into heat causing a rise in temperature at the distal end of the heating element in a region of the heating-element-to-conductor-wire connection 65 thereby melting/severing the coil securing suture 35 and hence releasing the embolic coil 5 at its desired location in the body. Thereafter, the corewire 45, insulated electrically conductive wire 60 and heating element 30 are withdrawn from the delivery catheter 80 by pulling in a proximal direction leaving in place the embolic coil 5 within the blood vessel at its desired treatment site.

The exemplary embodiment described above and illustrated in FIGS. 1A & 1B relates to a closed fiber detachment configuration since the proximal bead 40 of the coil securing suture 35 is enclosed/closed within the central lumen 33 of the helically wound coil of the heating element 30. In an alternative embodiment illustrated in FIG. 2A, the configuration of the heating element differs from that shown and described in FIGS. 1A & 1B in that the fiber detachment configuration is floating, that is, the proximal bead 40 is not enclosed within the central lumen 33 of the heating element 30. Such alternative embodiment depicted in FIG. 2A maximizes heat transfer to the coil securing suture 35 by minimizing the length (in an axial direction) of the helically wound coil heating element 30. Specifically, with this alternative embodiment, the number of loops/windings forming the helically wound coil of the heating element 30 (and hence the length in an axial direction of the heating element) is reduced in comparison to that of the first embodiment. This reduction in the number of loops/windings is realized by threading in a proximal direction back through the central lumen 33 of the helically wound coil of the heating element 30 a distal substantially straight trailing section. With this alternative embodiment the axial length of the heating element may be reduced to a range between approximately 1.0 mm to approximate 3.0 mm, preferably approximately 2 mm.

Additional design factors or considerations are contemplated other than that of maximizing heat transfer to the coil securing suture. On the one hand, the heating element 30 is desirably sufficiently long (as measured in an axial direction) to provide resistance when the embolic coil 5 is being implanted. While on the other hand, the length of the heating element 30 is sufficiently short to minimize micro-catheter kick back (i.e., push back out of aneurysm). A shorter length heating element also optimizes the desirable flexibility of the distal end of the coil delivery system.

Figure 2A:
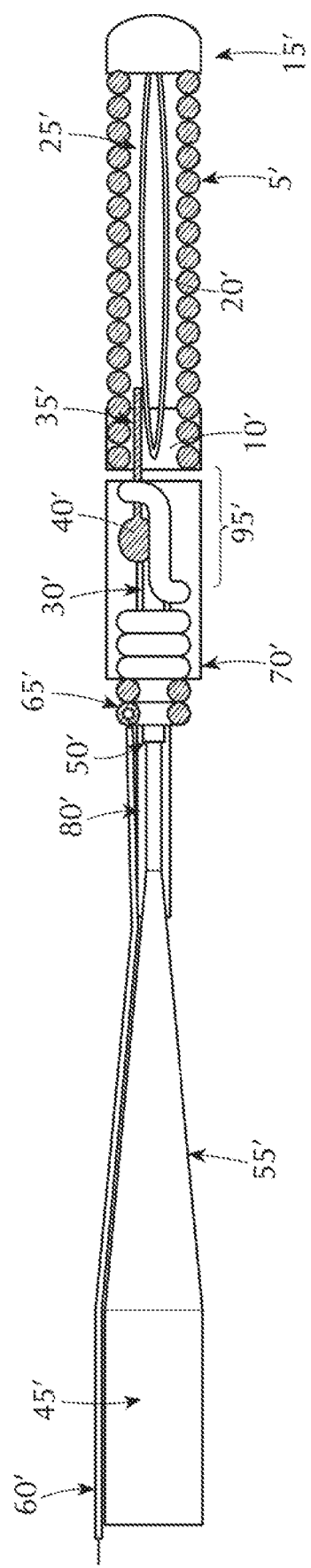
FIG. 2A is a cross-sectional view of a second embodiment of the present inventive heating detachment system for an embolic coil.
Figure 2B:
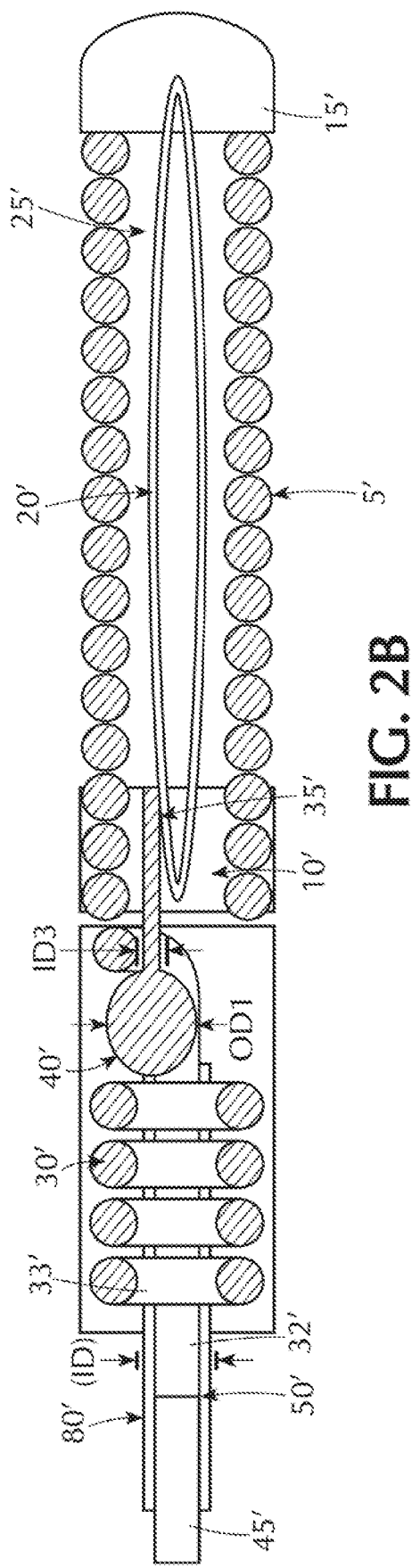
FIG. 2B is a cross-sectional view of the heating element and embolic coil in FIG. 2A illustrating that the coil securing suture proximal bead 40 has an outer diameter (OD1) larger than an inner diameter of the pre-formed heating element distal loop such that the coil securing suture proximal bead is retained therein.
Figure 2C:
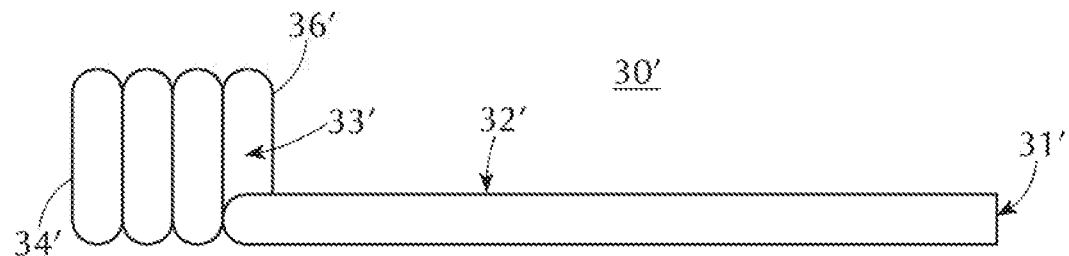
FIG. 2C is a side view of the helically wound coil heating element of FIG. 2A prior to the straight trailing section being fed back through its central lumen.
Figure 2D:
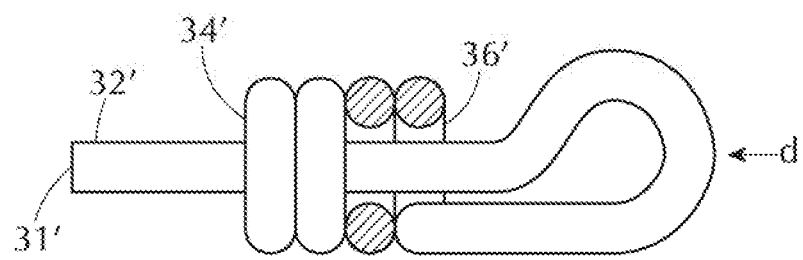
FIG. 2D is a partial cross-sectional view of the helically wound coil heating element of FIG. 2A after the straight trailing section has been bent into a primary distal loop.
Figure 2E:
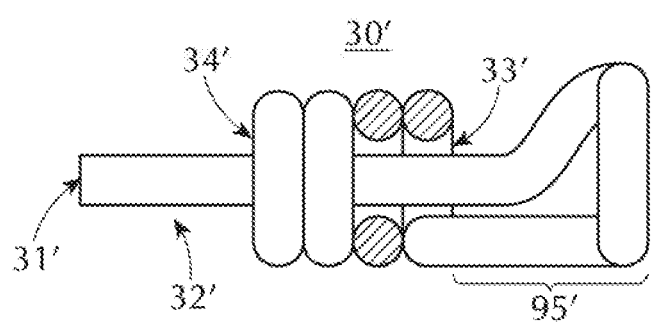
FIG. 2E is a partial cross-sectional view of the helically wound coil heating element of FIG. 2A after the primary loop has been bent approximately 90 degrees to form a secondary distal loop.

Referring to FIGS. 2A-2G directed to an exemplary second embodiment of the present invention, heating element 30' is a helically wound coil of a given resistivity that defines central lumen 33' extending axially between its substantially flush cut proximal end 34' and an opposite substantially flush cut distal end 36' (as shown in FIG. 2C). Extending beyond the distal end 36' of the windings, the coil forms a substantially straight trailing section 32' that finishes in a terminating end 31'. The terminating end 31' is bent backwards and threaded through the central lumen 33' of the helically wound coil towards its proximal end 34' forming a primary distal loop "d" (as depicted in FIG. 2D). The primary distal loop is disposed in a distal direction beyond the distal end 36' of the helically wound coil of the heating element 30', while the terminating end 31' of the trailing section 32' of the coil extends beyond the flush cut proximal end 34' of the helically wound coil. Next, the primary distal loop is then bent approximately 90 degrees from the axial plane of the helically wound coil to form a secondary distal loop (as illustrated in FIG. 2E). The resulting structure 95' is hereinafter referred to as a "pre-formed heating element distal loop." In designing the heating element in accordance with this second embodiment, the intent is to minimize the length (in an axial direction) of the pre-formed heating element distal loop 95' thereby minimizing the overall length (in an axial direction) of the heating element 30' and maximizing heat transfer to the coil securing suture 35'.

Figure 2F:
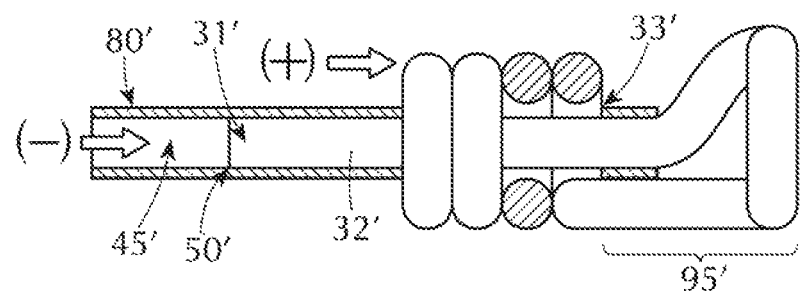
FIG. 2F is a partial cross-sectional top view of the helically wound coil heating element of FIG. 2E in which an insulation junction sleeve is disposed about the trailing section of coil extending in both the proximal and distal directions beyond the helically wound coil of the heating element to prevent electrical connection between the trailing section and the inner diameter (ID) of the central lumen of the helically wound coil.
Figure 2G:
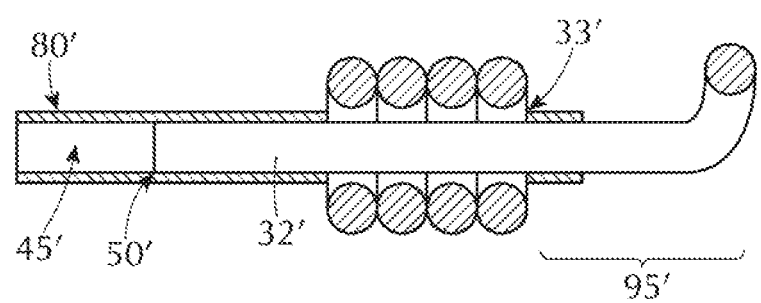
FIG. 2G is a partial cross-sectional side view of the helically wound coil heating element of FIG. 2E in which an insulation junction sleeve is disposed about the trailing section of coil extending in both the proximal and distal directions beyond the helically wound coil of the heating element to prevent electrical connection between the trailing section and the inner diameter (ID) of the central lumen of the helically wound coil.

Referring to FIGS. 2F & 2G, an insulation junction sleeve 80' is disposed about the trailing section 32' of coil extending in both the proximal and distal directions beyond the helically wound coil of the heating element to prevent electrical connection between the trailing section 32' and the inner diameter (ID) of the central lumen 33' of the helically wound coil. In addition, insulation junction sleeve 80' may also serve as a coupling to connect the distal end of the corewire 45' to the terminating end 31' of the heating element 30'.

As with the first embodiment, the heating element 30' in FIG. 2A is independent of the embolic coil 5' so that the two components may freely rotate 360 degrees about a common longitudinal axis extending axially through the two components. Rather than be directly connected (i.e., in direct physical contact) to one another, heating element 30' and embolic coil 5' are indirectly secured to one another via the coil securing suture 35' preferably made of a temperature sensitive polymer, disposed within the lumen 33' of the heating element 30'. A distal end of the coil securing suture 35' has a diameter sufficiently small to pass through the inner diameter (ID3) of the pre-formed heating element distal loop and extend beyond the distal end of the heating element 30' where it is embedded or otherwise secured via mechanical, adhesive or other means to a proximal coil junction 10' of the embolic coil 5'.

As depicted in FIG. 2B, on the opposite proximal end of the coil securing suture 35' is a proximal bead 40' freely movable within the pre-formed heating element distal loop 95'. The proximal bead 40' of the coil securing suture 35' is not connected, secured or attached in any way to the heating element 30'. Moreover, as illustrated in FIG. 2B, the coil securing suture proximal bead 40' has an outer diameter (OD1) that is larger than an inner diameter (ID3) of the pre-formed heating element distal loop 95; such that the coil securing suture proximal bead 40 is retained therein. Hence, proximal bead 40' prevents heating element 30' from separating from the embolic coil 5' until the coil securing suture 35' melts and severs or separates.

The configuration of the first embodiment illustrated in FIGS. 1A & 1B differs from that of the second embodiment shown in FIG. 2A in several other respects. In FIG. 1A the distal end of the corewire 45 is inserted into the proximal end of the heating element 30 and secured therein by a corewire-to-heating-element joint 50. Whereas in FIG. 2A, the distal end of corewire 45' is secured to the terminating end 31' of the coil at a location that extends in a proximal direction beyond the substantially flush proximal end 34' of the helically wound coil of the heating element 30'. Also, the location of connection of the distal end of the electrical conductor wire to the heating element differs in the two embodiments. In FIG. 1A, the heating-element-to-conductor-wire connection 65 is at the distal end of the helically wound coil of the heating element 30, whereas in FIG. 2A, the heating-element-to-conductor-wire connection 65' is at the proximal end of the helically wound coil of the heating element 30'. The location of heating-element-to-conductor-wire connection 65' along the resistive heating element 30' is dictated by the required resistance for the system. In all other respects the two embodiments are the same and thus reference is made to the detailed discussion above with respect to the first embodiment.

Figure 3A:
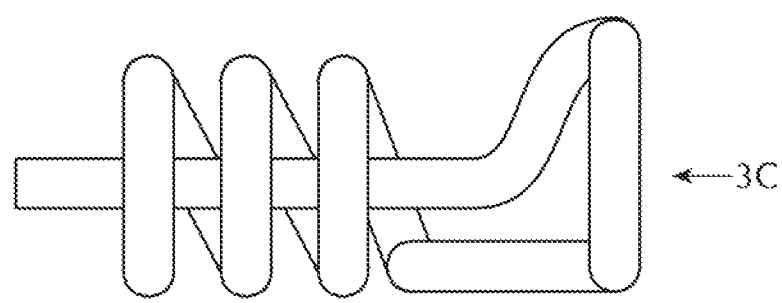
FIG. 3A is a top view of an alternative helically wound coil heating element in accordance with the second embodiment wherein adjacent loops/windings are separate a predetermined distance from one another.
Figure 3B:
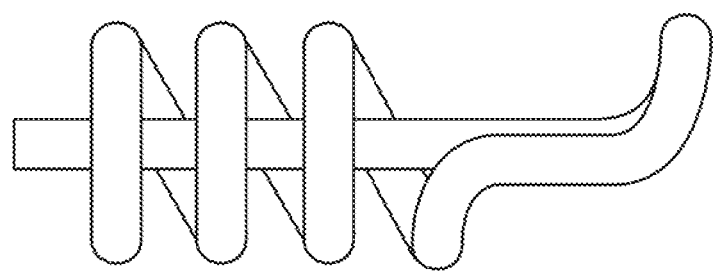
FIG. 3B is a side view of the exemplary helically wound coil heating element of FIG. 3A.
Figure 3C:
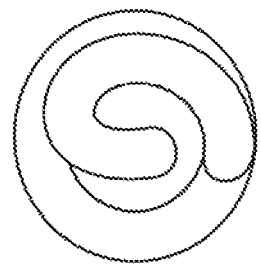
FIG. 3C is a front view of the exemplary helically wound coil heating element of FIG. 3A.

FIGS. 3A-3C depict top, side and front views, respectively, of an alternative helically wound coil heating element in accordance with the second embodiment wherein adjacent loops/windings are separated a predetermined distance from one another.

In accordance with the present invention, the corewire serves as one of the electrical conductors and the insulated electrically conductive wire as the other electrical conductor in forming a closed loop electrical path along with the power supply and heating element. Furthermore, the corewire also serves to advance the vaso-occlusive device in the delivery catheter. In response to current provided by the power supply a resistance is produced in the heating element that melts and/or severs the coil securing suture thereby releasing the embolic coil at a target site within the body.

The present invention has been shown and described for delivery and detachment of an embolic coil. Other vaso-occlusive devices are contemplated and within the scope of the present invention.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A vasculature occlusion device detachment system comprising:
   a heating element comprising a wound coil of a predetermined resistivity; the wound coil having a proximal end and an opposite distal end;
   a coil securing suture having a distal end and an opposite proximal end; the proximal end of the coil securing suture terminating in a proximal bead retained within the wound coil while the distal end of the coil securing suture extends beyond the distal end of the wound coil; the coil securing suture being rotatable, independently of the wound coil, 360 degrees about a longitudinal axis extending therethrough the wound coil;
   an electrically conductive corewire having a proximal end and an opposite distal end; the distal end of the electrically conductive corewire being connected to the proximal end of the wound coil; and
   an insulated electrically conductive wire separate from the electrically conductive corewire; the insulated electrically conductive wire having a proximal end and an opposite distal end; the distal end of the insulated electrically conductive wire being secured to the wound coil at a wound coil to conductive wire connection.

2. The system in accordance with claim 1, further comprising a power source electrically connected to the respective proximal ends of the electrically conductive corewire and the insulated electrically conductive wire.

3. The system in accordance with claim 1, wherein the coil securing suture is made of a temperature sensitive polymer.

4. The system in accordance with claim 1, wherein the electrically conductive corewire is tapered from its proximal end towards is distal end.

5. The system in accordance with claim 1, further comprising a vasculature occlusion device having a proximal end and an opposite distal end; the distal end of the coil securing suture being secured to the proximal end of the vasculature occlusion device; the wound coil being independently rotatable relative to that of the vasculature occlusion device 360 degrees about a longitudinal axis of the wound coil.

6. The system in accordance with claim 1, wherein the electrically conductive corewire does not have a lumen defined therein.

7. The system in accordance with claim 1, wherein a non-conductive coating is disposed on an exterior surface of the electrically conductive corewire.

8. The system in accordance with claim 1, wherein an axial length of the wound coil is in a range between approximately 1 mm and approximately 3 mm.

9. A method of using the vasculature occlusion device detachment system in accordance with claim 1, comprising the steps of:
   securing the distal end of the coil securing suture to a proximal end of a vasculature occlusion device;
   advancing the vasculature occlusion device via a delivery catheter through a human body using the electrically conductive corewire;
   positioning the vasculature occlusion device at a target site the human body;
   applying an electrical current powered by a power source to the electrically conductive corewire and insulated electrically conductive wire;
   as a result of the applied electrical current, increasing a resistance of the wound coil in a region of the wound coil to conductive wire connection;

generating sufficient heat due to the increased resistance to melt and sever the coil securing suture at the region proximate the wound coil to conductive wire connection thereby releasing the vasculature occlusive device from the wound coil; and withdrawing from the human body by pulling in a proximal direction the delivery catheter, the wound coil and the electrically conductive corewire, while leaving at the target site in the human body the vasculature occlusive device.

10. The method in accordance with claim 9, wherein the wound coil being independently rotatable relative to that of the vasculature occlusion device 360 degrees about a longitudinal axis extending axially through the wound coil and vasculature occlusion device.

11. A vasculature occlusion device detachment system comprising:

a heating element of a predetermined resistivity; the heating element having a proximal end and an opposite distal end;

a coil securing suture having a distal end and an opposite proximal end; the proximal end of the coil securing suture terminating in a proximal bead retained within the heating element while the distal end of the coil securing suture extends beyond the distal end of the heating element; the coil securing suture being rotatable, independently of the heating element, 360 degrees about a longitudinal axis extending therethrough the heating element;

an electrically conductive corewire having a proximal end and an opposite distal end; the distal end of the electrically conductive corewire being connected to the proximal end of the heating element; and an insulated electrically conductive wire separate from the electrically conductive corewire; the insulated electrically conductive wire having a proximal end and an opposite distal end; the distal end of the insulated electrically conductive wire being secured to the heating element at a heating element to conductive wire connection;

wherein the heating element is a helically wound coil comprising a plurality of windings forming a central lumen extending longitudinally therethrough from a proximal end to a distal end of the helically wound coil; wherein an inner diameter of the helically wound coil at its proximal end is greater than an inner diameter of the helically wound coil at its distal end; the proximal bead having an outer diameter smaller than the inner diameter of the helically wound coil at its proximal end; and the proximal bead of the coil securing suture being freely movable in an axial direction within the central lumen of the helically wound coil but retained at the distal end of the helically wound coil by its smaller inner diameter relative to the outer diameter of the proximal bead.

12. The system in accordance with claim 11, wherein the distal end of the insulated electrically conductive wire is connected to the distal end of the helically wound coil.

* * * * *